(12) United States Patent
Lau et al.

(10) Patent No.: US 6,527,789 B1
(45) Date of Patent: Mar. 4, 2003

(54) STENT DELIVERY SYSTEM

(75) Inventors: Lilip Lau, Cupertino; William M. Hartigan, Fremont, both of CA (US); Farhad Khosravi, Boston, MA (US); Kurt R. Klemm, Santa Clara, CA (US); Ulrich Sigwart, Morges (CH)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/312,428

(22) Filed: May 14, 1999

Related U.S. Application Data

(60) Division of application No. 09/136,982, filed on Aug. 20, 1998, which is a division of application No. 09/119,344, filed on Jul. 20, 1998, now Pat. No. 6,113,607, which is a division of application No. 08/630,528, filed on Apr. 10, 1996, now Pat. No. 5,782,855, which is a division of application No. 08/085,959, filed on Jul. 6, 1993, now Pat. No. 5,507,768, which is a continuation-in-part of application No. 07/647,464, filed on Jan. 28, 1991, now abandoned.

(51) Int. Cl.⁷ .............................................. A61M 29/00
(52) U.S. Cl. ........................................................ 606/194
(58) Field of Search ........................................ 606/194

(56) References Cited

U.S. PATENT DOCUMENTS 4,748,982 A * 6/1988 Horzewski et al.
4,762,128 A * 8/1988 Rosenbluth
4,893,623 A * 1/1990 Rosenbluth

FOREIGN PATENT DOCUMENTS

| EP | 0 408 245 A1 | * | 1/1991 |
| JP | 62-213762 | * | 9/1987 |
| JP | 63-214264 | * | 9/1988 |
| JP | 63-246178 | * | 10/1988 |
| JP | 3-57465 | | 3/1991 |

OTHER PUBLICATIONS

"Seven Years Development and Application of the Sliding Rail System (Monorail) for PTCA" from The Practice of Interventional Cardiology, Second Edition, published in 1993.

* cited by examiner

Primary Examiner—William E. Kamm
Assistant Examiner—Jeffrey R. Jastrzab
(74) Attorney, Agent, or Firm—Fulwider Patton Lee & Utecht, LLP

(57) ABSTRACT

A stent delivery assembly includes a catheter for carrying an intravascular stent for use in a body lumen. The catheter assembly includes a rapid exchange feature in which a proximal port is spaced a relatively short distance form the distal end of the catheter and a relatively long distance from the proximal end of the catheter. A stent is mounted on the expandable member or balloon portion of the catheter.

23 Claims, 3 Drawing Sheets

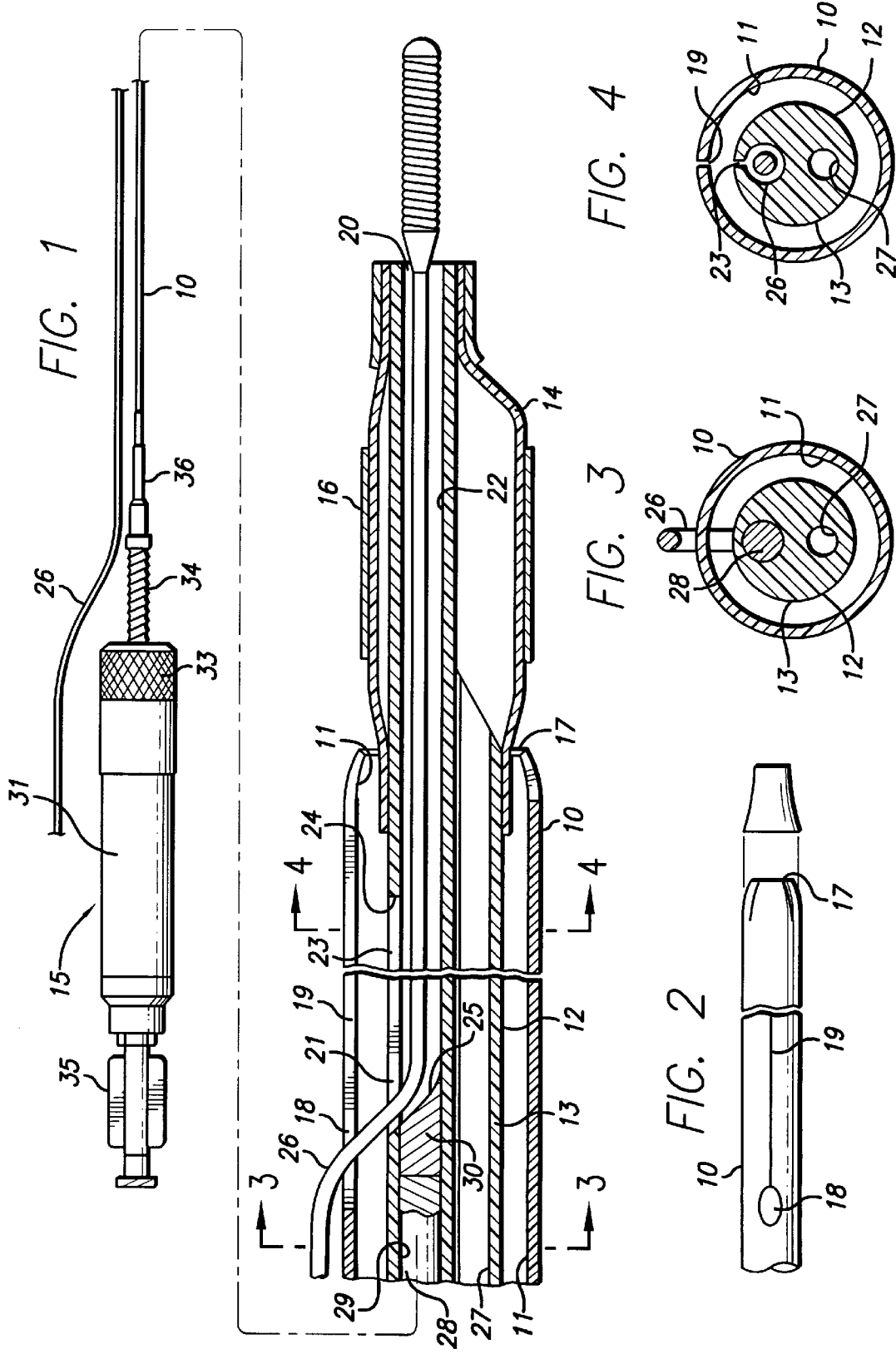

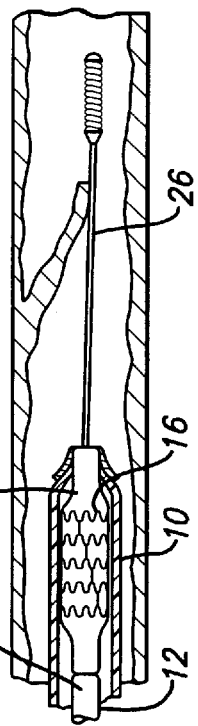
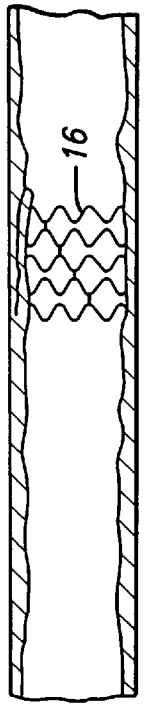
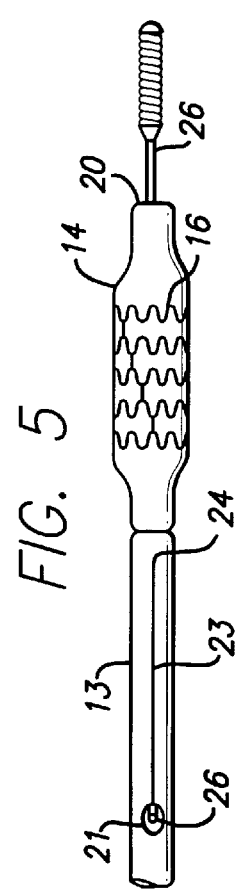
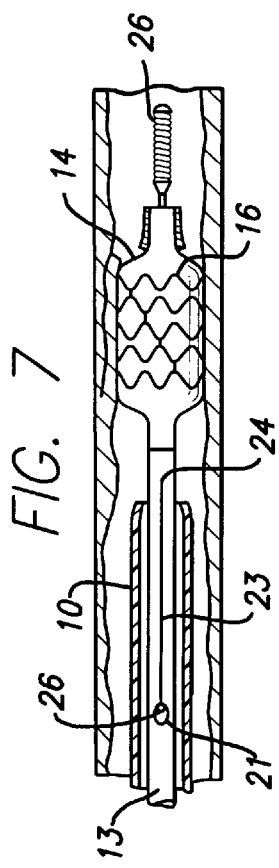
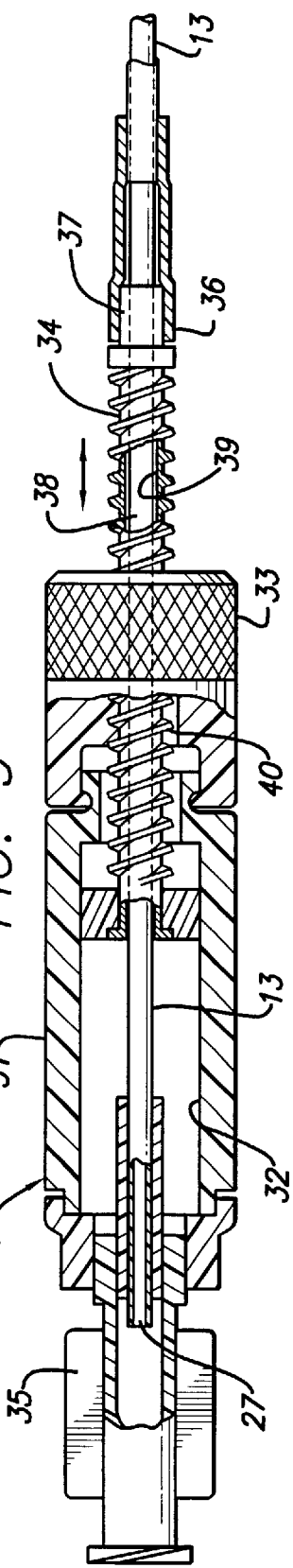

STENT DELIVERY SYSTEM

RELATED APPLICATION

This application is a division of U.S. Ser. No. 09/136,982 filed Aug. 20, 1998 which is a division of U.S. Ser. No. 09/119,344 filed Jul. 20, 1998 now U.S. Pat. No. 6,113,607, which is a division of U.S. Ser. No. 08/630,528 filed Apr. 10, 1996, now U.S. Pat. No. 5,782,855, which is a division of U.S. Ser. No. 08/085,959 filed Jul. 6, 1993, now U.S. Pat. No. 5,507,768, which is a continuation-in-part application of U.S. Ser. No. 07/647,464 filed on Jan. 28, 1991, now abandoned.

BACKGROUND OF THE INVENTION

This invention relates to devices for the treatment of heart disease and particularly to endo-arterial prosthesis, which are commonly called stents.

Several interventional treatment modalities are presently used for heart disease including balloon and laser angioplasty, atherectomy and by-pass surgery.

In typical balloon angioplasty procedures, a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon which is made of relatively inelastic materials, is inflated to a predetermined size with radiopaque liquid at relatively high pressure (e.g., greater than 4 atmospheres) to compress the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guidewires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); and U.S. Pat. No. 4,748,982 (Horzewski, et al.) which are hereby incorporated herein in their entirety by reference thereto.

A major problem which can occur during balloon angioplasty procedures is the formation of intimal flaps which can collapse and occlude the artery when the balloon is deflated at the end of the angioplasty procedure. Another major problem characteristic of balloon angioplasty procedures is the large number of patients which are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient is put in an extremely dangerous situation requiring immediate medical attention, particularly in the coronary arteries.

A major focus of recent development work in the treatment of heart disease has been directed to endoprosthetic devices called stents. Stents are generally cylindrically shaped intravascular devices which are placed within a damaged artery to hold it open. The device can be used to prevent restenosis and to maintain the patency of blood vessel immediately after intravascular treatments. In some circumstances, they can also be used as the primary treatment device where they are expanded to dilate a stenosis and then left in place.

However, the rapid and effective delivery of a stent to the desire location within the patient's vasculature has been found to be difficult, particularly in those situations in which an intimal flap has occluded an artery. Attempts to advance a stent into regions of coronary arteries occluded by dissected arterial linings have not been very successful.

The two basic methods and systems have been developed for delivering stents to desired locations within body lumens. One method and system involves compressing or otherwise reducing the diameter of an expandable stent, disposing the compressed stent within a lumen provided in the distal end of a tubular catheter, advancing the catheter through the patient's vasculature until the distal end of the catheter is immediately adjacent to the desired vascular location and then pushing the stent out the distal end of the catheter into the desired location. Once out of the catheter, the compressed stent expands or is expanded to thereby hold open the artery or other body lumen into which it is placed.

Another method and system involves disposing a compressed or otherwise small diameter stent about an expandable member such as a balloon on the distal end of a catheter, advancing the catheter through the patient's vascular system until the stent is in the desired location within a blood vessel and then expanding the expandable member on the catheter to expand the stent within the blood vessel. The expanded expandable member is then contracted and the catheter withdrawn, leaving the expanded stent within the blood vessel, holding open the passageway thereof.

The following references illustrate various types of stents and stent delivery systems. The list is meant to be exemplary, not exhaustive on the subject.

U.S. Pat. No. 3,868,956
U.S. Pat. No. 4,503,569
U.S. Pat. No. 4,512,338
U.S. Pat. No. 4,553,545
U.S. Pat. No. 4,560,374
U.S. Pat. No. 4,655,771
U.S. Pat. No. 4,665,918
U.S. Pat. No. 4,733,665
U.S. Pat. No. 4,760,849
U.S. Pat. No. 4,762,128
U.S. Pat. No. 4,768,507
U.S. Pat. No. 4,795,458
U.S. Pat. No. 4,800,882
U.S. Pat. No. 4,830,003
U.S. Pat. No. 4,856,516
U.S. Pat. No. 4,878,906
U.S. Pat. No. 4,886,062
U.S. Pat. No. 4,907,336
U.S. Pat. No. 4,913,141
U.S. Pat. No. 4,923,464
U.S. Pat. No. 4,950,227

What has been needed and heretofore unavailable is a stent delivery system which can be quickly and easily used in a wide variety of situations and particularly in emergency situations where a dissected arterial lining has collapsed and has occluded the flow of blood to a vital organ. The present invention satisfies this need.

SUMMARY OF THE INVENTION

This invention is directed to an improved stent delivery system which can quickly and easily position a stent into an occluded region of a blood vessel.

The stent delivery system of the invention includes an elongated sheath having an inner lumen extending therein, a first port in its distal end which is adapted to receive a guidewire and a second port spaced proximally from the distal end of the delivery sheath which is also adapted to receive a guidewire, both of the ports being in fluid communication with the inner lumen of the sheath. The delivery system also includes an intravascular catheter slidably disposed within the inner lumen of the delivery sheath, the catheter having an expandable member on the distal extremity thereof, such as an inflatable balloon, which is adapted to receive an expandable stent on the exterior thereof. The catheter has a first port in its distal end adapted to receive a guidewire and a second port spaced proximally from the distal end of the catheter adapted to receive a guidewire, with both of these ports being in communication with an inner lumen extending within the interior of the catheter. The second guidewire receiving port should be spaced proximally from the expandable member on the distal extremity of the catheter. Means may be provided to adjust the relative axial positions of the catheter and sheath to expose the expandable stent on the expandable member of the catheter so that the stent can be expanded against the blood vessel wall by expanding the expandable member.

Preferably, both the delivery sheath and the intravascular catheter have slits in the walls, thereof which extend distally from their proximal ports to facilitate the removal of these devices from the guidewire upon the withdrawal of the delivery system from the patient's vascular system after the delivery of a stent.

In a typical situation, the guidewire used to deliver a dilatation catheter through the patient's vascular system to a stenotic region therein is left disposed within the patient after the dilatation catheter has been removed therefrom. To maintain access to the stenotic region, the distal end of the guidewire should be left crossing the stenotic region where the stent is to be placed. The proximal end of the guidewire, which extends out of the patient, is inserted through the port in the distal end of the intravascular catheter which has a stent mounted on the expandable member. The intravascular catheter is disposed within the inner lumen of the delivery sheath with the distal end of the catheter extending out the port in the distal end of the delivery sheath to facilitate the insertion of the proximal end of the guidewire. The relative axial position between the delivery sheath and intravascular catheter is adjusted so that the expandable member on the distal extremity of the intravascular catheter with the expandable stent mounted thereon is pulled back into the inner lumen of the delivery sheath. The delivery sheath and the catheter therein are then advanced through the patient's vascular system, preferably over a guide wire which extends rom outside the patient to the ostium of the desired coronary artery, over a guidewire which extends from outside the patient to the ostium of the desired coronary artery, until the stent mounted on the expandable member of the intravascular catheter is positioned within the stenotic region of the patient's blood vessel.

The relative axial positions of the delivery sheath and the intravascular catheter having the stent thereon is adjusted to urge the distal end of the vascular catheter out of the distal end of the sheath to expose the expandable stent. Either the catheter can be advanced distally with respect to the sheath or the sheath can be withdrawn proximally with respect to the catheter or both movements can be employed. Once the stent is completely out of the delivery sheath, the expandable member on the intravascular catheter can be expanded to expand the stent against stenotic mass within the blood vessel. After expanding the stent, the expandable member on the vascular catheter is contracted so that the catheter can be removed from the patient's blood vessel, leaving the expanded stent in its desired position therein.

The delivery sheath and the intravascular catheter may be withdrawn together or the sheath may be withdrawn first followed by withdrawal of the catheter. They are removed over the guide wire until the proximal guide wire port on the sheath and/or the catheter exits the proximal end of the guiding catheter, the sheath and the catheter can be peeled away from the guidewire with the guidewire sliding through the slits which extend distally from the proximal ports thereof. The sheath and the intravascular catheter are pulled proximally out of the proximal end of the guiding catheter a sufficient distance to expose the guide wire. The exposed section of the guidewire is secured, e.g., manually held, in place so that the sheath and the intravascular catheter can be pulled off the proximal end of the guidewire.

The delivery system of the invention can effectively deliver a stent to a desired location within a patient's blood vessel, it can allow the stent to be secured within the desired location, and it can be easily and quickly removed. These and other advantages of the invention will become more apparent from the following detailed description of the invention, when taken in conjunction with the accompanying exemplary drawings.

BRIEF DESCRIPTION OF THE DRAWINGS

FIG. 1 is a partial longitudinal cross-sectional view of a stent delivery system which embodies features of the invention.

FIG. 2 is a top view of the delivery sheath shown in FIG. 1.

FIG. 3 is a transverse cross-sectional view taken along the lines 3—3 shown in FIG. 1.

FIG. 4 is a transverse cross-sectional view taken along the lines 4—4 shown in FIG. 1.

FIG. 5 illustrates a stent mounted on the outer surface of a balloon of the intravascular catheter shown in FIG. 1.

FIG. 6 illustrates the advancement of the stent delivery system shown in FIG. 5 into an artery which has been damaged by an intravascular procedure such as an angioplasty FIG. 7 illustrates the inflation of the balloon on the intravascular catheter shown in FIG. 1 which expands the stent mounted on the exterior thereof FIG. 8 illustrates the expanded stent disposed within a damaged arterial section maintaining the patency thereof.

FIG. 9 is a partial cross-sectional view of the manipulator shown in FIG. 1.

DETAILED DESCRIPTION OF THE INVENTION

Figure 10:
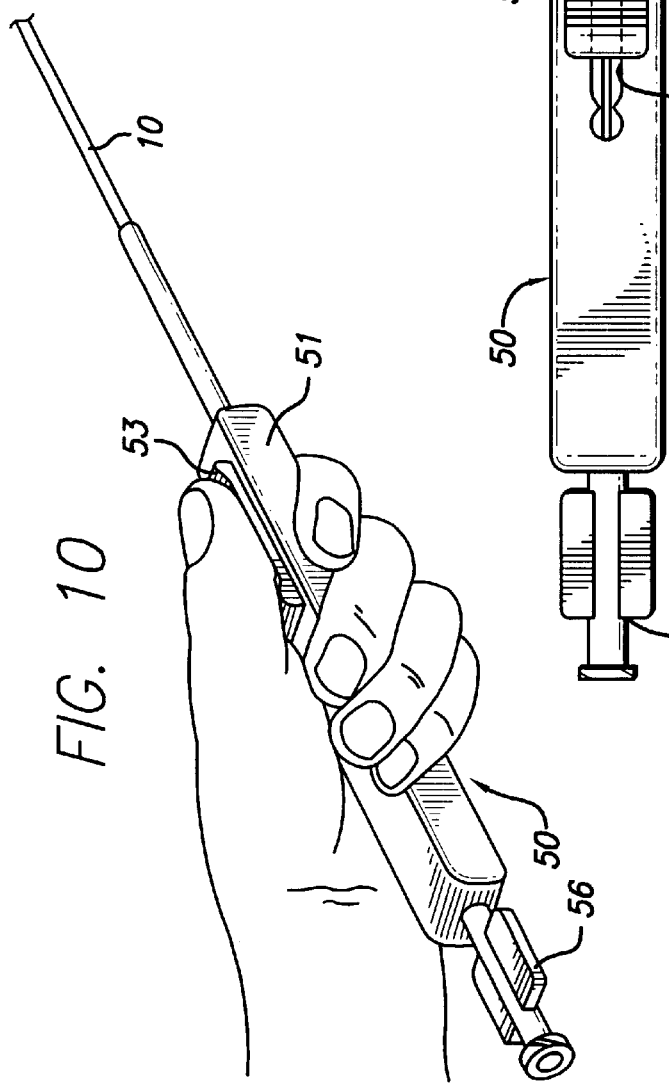
FIG. 10 is a perspective view of an alternative manipulator mounted on the proximal end of the delivery system shown in FIG. 1.

FIGS. 1–4 illustrate a stent delivery system which embodies features of the invention. Generally, the delivery system includes a delivery sheath 10 which has an inner lumen 11 and an intravascular catheter 12 disposed within the outer lumen 11. The intravascular catheter has an elongated catheter body 13 and a balloon 14 on the distal portion of the catheter body. A manipulating device 15 is provided on the distal end of the delivery system which is employed to effect relative axial or longitudinal movement between the delivery sheath 10 and the intravascular catheter 12. An expandable stent 16, which is to be delivered within a patient's body lumen, is mounted on the exterior of the balloon 14.

The delivery sheath 10 has a distal port 17 in its distal end which is in fluid communication with the outer lumen 11 and a proximal port 18 disposed proximally to the distal port. The distal portion of delivery sheath 10 tapers down in a spherical-like manner so that the cross-sectional area is somewhat less in the distal region than the cross-sectional area of the rest of the delivery sheath. A slit 19 extends from the proximal port 18 to the distal port 17. In one embodiment, a plurality of slits 59 in the wall of sheath 10 extend a short distance from the distal port 17. As contemplated, the slits 59 would facilitate in the relative axial position adjustment of the sheath 10 and intravascular catheter 12.

The intravascular catheter 12 has a distal port 20 and a proximal port 21 which are in fluid communication with a first inner lumen 22 extending within the distal portion of the catheter 12 and being adapted to slidably receive a guidewire therein. A slit 23 extends from the proximal port 21 to a location 24 proximal to the proximal end of balloon 14. The proximal end of the guidewire receiving first inner lumen 22 is provided with a ramp 25 to guide the proximal end of guidewire 26 out the proximal port 21 of intravascular catheter 12 when the catheter is mounted onto the guidewire, as will be discussed hereinafter. A second, much longer inner lumen 27 is provided within the catheter body 13 to direct inflation fluid from the proximal end of the catheter body to the interior of the balloon 14.

Proximal to the proximal port 21 in the catheter body 13 is a stiffening member 28 which is disposed in third inner lumen 29 provided within the catheter body 13. As shown in the drawings, the third inner lumen 29 and the first inner lumen 22 may be the same lumen with a plug 30 separating the two lumens. The ramp 25 is on the distal side of the plug 30.

As illustrated in FIGS. 1 and 9, the manipulator 15 on the proximal end of the delivery system has a housing 31 with an interior chamber 32, a cap 33 rotatably mounted onto the distal end of the housing 31, an elongated drive member 34 which has male threads on the exterior, thereof and which is at least partially disposed within the interior chamber 32 and a Luer lock 35 which is fixed within the proximal end of the housing 31. The proximal end 36 of the sheath 10 is secured to the distal end 37 of the elongated drive member 34 which extends out of the distal end of the housing 31. As shown in more detail in FIG. 9, the proximal end 38 of the catheter body 13 passes through passageway 39 in the elongated drive member 34 and is fixed within the Luer lock 35 by suitable means such as adhesive. The cap 33 which is rotatably mounted onto the distal end of the housing 31 is provided with an inner threaded collar 40 adapted to threadably engage the threaded exterior of the elongated driving member 34. Rotation of the cap 33 moves the driving member 34 axially to thereby effect relative axial movement between the sheath 10 and the intravascular catheter 12.

In a typical situation, the stent delivery system of the invention is used after an intravascular procedure has damaged a patient's arterial lining to such an extent that the lining needs support to prevent it from collapsing into the arterial passageway and thereby preventing sufficient blood flow through the blood vessel. In these situations there will usually be a guidewire 26 (or other guiding member) in place extending across the damaged section of the artery such as shown in FIG. 6. The proximal end of the guidewire 26, which extends out of the patient during the entire procedure, is then inserted through the distal port 20 in the distal end of the catheter 12 and advanced proximally through the first inner lumen 22 until the proximal end of the guidewire impacts the ramp 25 and is thereby directed through the proximal port 21.

The intravascular catheter 12 is preferably positioned within the inner lumen 11 of the delivery sheath 10 so that at least a significant portion of the proximal port 18 in the sheath is in alignment with the proximal port 21 of the intravascular catheter. In this manner, proximal advancement of the guidewire 26 through the inner lumen 22 will also direct the proximal end of the guidewire out the proximal port 18 in the delivery sheath 10. The proximal end of the guidewire 26 may then be manually held to maintain the position of the guidewire within the patient's vasculature, while the stent delivery system is advanced over the guidewire and through the patient's vascular system. The advancement of the stent delivery system continues until the distal ends of the catheter and sheath extend adjacent to or across the damaged arterial site. Next, the manipulator 15 on the proximal end of the delivery system is actuated by rotating the cap 33 on the proximal end of the housing 31 to move the sheath 10 proximally with respect to the catheter 12 and thereby expose the stent 16 mounted on the balloon 14. When the balloon and the stent mounted thereon are properly placed within the damaged artery, inflation fluid is directed under substantial pressure through the Luer lock 35 and the inflation lumen 27 in the catheter body 13 to the interior of the balloon 14, expanding the balloon and simultaneously expanding the stent 16 against the blood vessel wall as shown in FIG. 7. The delivery system, both the sheath 10 and the catheter 12, may then be removed from the patient along with the guidewire 26, leaving the expanded stent 16 within the damaged arterial section as shown in FIG. 8 to maintain the patency thereof.

The housing 31 of the manipulator 15 can be held in the palm of the physician's hand, with the thumb and index finger thereof used to rotate cap 33 and thereby cause the necessary relative motion between the sheath 10 and intravascular catheter 12 to expose the stent 16 mounted on the balloon 14. The physician can operate an inflation device, such as described in U.S. Pat. No. 4,439,185, with his or her free hand to inject inflation fluid through Luer lock 35 into the interior of the balloon 14 to inflate the balloon and thereby expand the stent 16 while holding the delivery system in place with the other hand. Upon deflating the balloon 14, the manipulator 15 can again be actuated by the physician rotating cap 33 with the fingers of the hand holding the manipulator 15, to cause relative rotation between the intravascular catheter 12 and the sheath 10, to pull the intravascular catheter 12 back into the distal end of the sheath 10 (or pushing the distal end of the sheath over the distal end of the intravascular catheter 12, depending upon the perspective). The entire assembly, including the guidewire 26, can then be removed from the patient.

Figure 11:
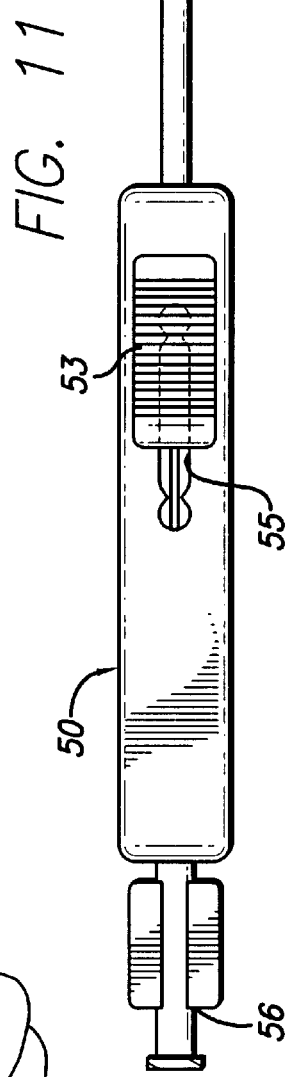
FIG. 11 is a plan view of the manipulator shown in FIG. 10.
Figure 12:
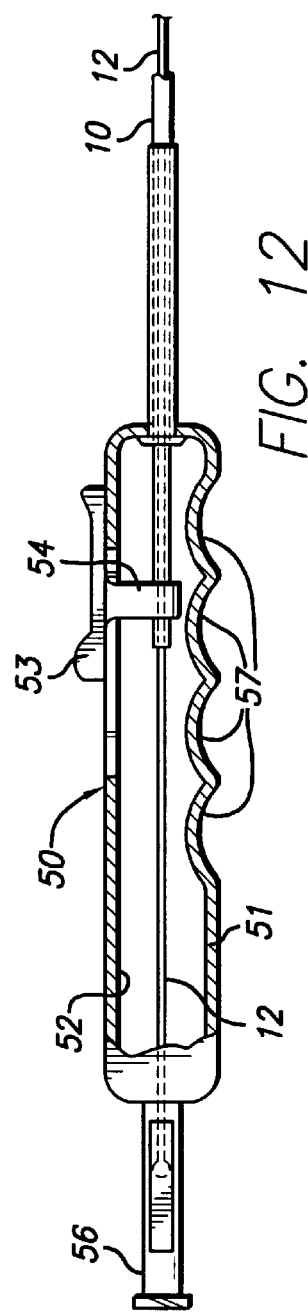
FIG. 12 is an elevational view, partially in section, of the manipulator shown in FIG. 10.

The alternative manipulator 50 illustrated in FIGS. 10–12 generally includes a housing 51 with an interior chamber 52 and a slidable element 53 with a depending portion 54 which extends through a slot 55 in the wall of the housing and is secured to the proximal end of the sheath 10 which extends through an opening provided in the distal end of the housing. The catheter 12 extends out the proximal end of the sheath 10, out an opening in the proximal end of the housing 51 and into a Luer lock 56 secured to the proximal end of the housing. The proximal end of the catheter 12 is secured within the Luer lock 56 to be in fluid communication with the inner inflation lumen 27 of the catheter so that inflation fluid can be injected through the Luer lock to the interior of the balloon 14 on the catheter to expand the balloon and the stent 16 mounted thereon. As is evident from FIG. 10, movement from element 53 on the exterior of the housing 51 will effect the relative axial movement between the delivery sheath 10 and the catheter 12 required to expose the stent 16 mounted on the balloon 14. The slot 55 has narrowed portions near both ends thereof which have widths just slightly smaller than the depending element 54 so that the position of the slidable element 53 can be locked. The underside of the housing 51 may be provided with undulated surface 57 which is adapted to receive the fingers of an operator to facilitate the gripping thereof.

The dimensions of the intravascular catheter will generally follow the dimensions of intravascular catheters used in angioplasty procedures in the same arterial location. Typically, the length of a catheter for use in the coronary arteries is about 150 cm, the outer diameter of the catheter shaft is about 0.035 inch (0.89 mm), the length of the balloon is typically about 2 cm and the inflated diameter about 1 to about 8 mm.

The materials of construction may be selected from those used in conventional balloon angioplasty catheters, such as those described in the patents incorporated by reference. The delivery sheath will generally be slightly shorter than the intravascular catheter, e.g., by about the length of the manipulating device 15 or 50, with an inner diameter large enough to accommodate the intravascular catheter and to allow the catheter free longitudinal movement therein. The sheath and the catheter shaft can be made of conventional polyethylene tubing.

While the present invention has been described herein in terms of delivering an expandable stent to a desired location within a patient's blood vessel, the delivery system can be employed to deliver stents to locations within other body lumens such as urethra or Fallopian tubes so that the stents can be expanded to maintain the patency of these body lumens. Various changes and improvements may also be made to the invention without departing from the scope thereof.

What is claimed is:

1. An intravascular stent delivery assembly, comprising:
   a. a catheter having:
      i. a proximal end and a distal end;
      ii. a distal port at the distal end;
      iii. a proximal port spaced a relatively short distance from the distal end and a relatively long distance from the proximal end;
      iv. a passageway for a guide wire extending between the distal port and the proximal port; and
      v. an expandable member for expanding a stent; and
   b. a stent disposed about the expandable member.
2. The assembly of claim 1, wherein the stent is mounted on the expandable member.
3. The assembly of claim 1, wherein the stent is longitudinally flexible and expandable and comprises a plurality of cylindrical elements which are independently expandable in the radial direction and which are interconnected so as to be generally aligned on a common longitudinal axis.
4. The assembly of claim 3, wherein the cylindrical elements of the stent are out of phase.
5. The assembly of claim 1, wherein the expandable member comprises a balloon.
6. The assembly of claim 1, wherein the catheter has an inflation passageway.
7. The assembly of claim 6, wherein the inflation passageway is in fluid communication with the balloon.
8. The assembly of claim 1, further comprising a sheath having a passageway for receiving the catheter.
9. The assembly of claim 8, wherein the sheath has a first port at a distal end of the sheath and a second port spaced distally of the proximal end of the sheath.
10. The assembly of claim 9, wherein a slit in the sheath extends distally from the second port so that the guide wire can be pulled through the slit during catheter exchanges.
11. The assembly of claim 1, wherein a slit in the catheter extends distally from the proximal port so that the guide wire can be pulled through the slit during catheter exchanges.
12. An intravascular stent delivery assembly comprising:
    a. a catheter having
       i. a proximal end and a distal end;
       ii. a distal port at the distal end;
       iii. a proximal port spaced a relatively short distance from the distal end and a relatively long distance from the proximal end;
       iv. a passageway for a guide wire extending between the distal port and the proximal port;
       v. a long relatively stiff proximal section;
       vi. a short relatively flexible distal section; and
       vii. an expandable member for expanding a stent; and
    b. a stent disposed about the expandable member.
13. The assembly of claim 12, wherein the stent is mounted on the expandable member.
14. The assembly of claim 12, wherein the stent is longitudinally flexible and expandable and comprises a plurality of cylindrical elements which are independently expandable in the radial direction and which are interconnected so as to be generally aligned on a common longitudinal axis.
15. The assembly of claim 14, wherein the cylindrical elements of the stent are out of phase.
16. The assembly of claim 12, wherein a stiffening mandrel is disposed within at least the proximal section of the catheter.
17. The assembly of claim 12, wherein the expandable member comprises a balloon.
18. The assembly of claim 17, wherein the catheter has an inflation passageway.
19. The assembly of claim 18, wherein the inflation passageway is in fluid communication with the balloon.
20. The assembly of claim 12, further comprising a sheath having a passageway for receiving the catheter.
21. The assembly of claim 20, wherein the sheath has a first port at a distal end of the sheath and a second port spaced distally of the proximal end of the sheath.
22. The assembly of claim 21, wherein a slit in the sheath extends distally from the second port so that the guide wire can be pulled through the slit during catheter exchanges.

23. The assembly of claim 12, wherein a slit in the catheter extends distally from the proximal port so that the guide wire can be pulled through the slit during catheter exchanges.

* * * * *

UNITED STATES PATENT AND TRADEMARK OFFICE
CERTIFICATE OF CORRECTION

PATENT NO. : 6,527,789 B1                                              Page 1 of 1
DATED      : March 4, 2003
INVENTOR(S) : Lilip Lau et al.

It is certified that error appears in the above-identified patent and that said Letters Patent is hereby corrected as shown below:

<u>Title page,</u>
Item [75], Inventors, after 2nd inventor's residence, delete the semicolon ";" and the following three inventors.
Item [57], ABSTRACT,
Line 4, change "form", to read -- from --.

<u>Column 3,</u>
Line 62, change "rom", to read -- from --.

<u>Column 4,</u>
Lines 54 and 57, add a period -- . -- after last word of each line.

<u>Column 5,</u>
Line 19, change "outer", to read -- inner --.
Lines 21 through 24, delete entire sentence beginning with "The" and ending with "sheath.".
Lines 25 through 30, delete entire sentence beginning with "In" and ending with "12.".

Signed and Sealed this

Twenty-second Day of July, 2003

JAMES E. ROGAN
*Director of the United States Patent and Trademark Office*

(12) EX PARTE REEXAMINATION CERTIFICATE (7333rd)
United States Patent
Lau et al.

(10) Number: US 6,527,789 C1
(45) Certificate Issued: Jan. 26, 2010

(54) STENT DELIVERY SYSTEM

(75) Inventors: Lilp Lau, Cupertino, CA (US); William M. Hartigan, Fremont, CA (US); Farhad Khosravi, Boston, MA (US); Kurt R. Klemm, Santa Clara, CA (US); Ulrich Sigwart, Morges (CH)

(73) Assignee: Advanced Cardiovascular Systems, Inc., Santa Clara, CA (US)

Reexamination Request:
No. 90/009,311, Oct. 29, 2008

Reexamination Certificate for:
Patent No.: 6,527,789
Issued: Mar. 4, 2003
Appl. No.: 09/312,428
Filed: May 14, 1999

Certificate of Correction issued Jul. 22, 2003.

Related U.S. Application Data

(60) Division of application No. 09/136,982, filed on Aug. 20, 1998, now abandoned, which is a division of application No. 09/119,344, filed on Jul. 20, 1998, now Pat. No. 6,113,607, which is a division of application No. 08/630,528, filed on Apr. 10, 1996, now Pat. No. 5,782,855, which is a division of application No. 08/085,959, filed on Jul. 6, 1993, now Pat. No. 5,507,768, which is a continuation-in-part of application No. 07/647,464, filed on Jan. 28, 1991, now abandoned.

(51) Int. Cl.
*A61M 29/00* (2006.01)

(52) U.S. Cl. ...................................... 606/194

(58) Field of Classification Search .................. None
See application file for complete search history.

(56) References Cited

U.S. PATENT DOCUMENTS

| 4,733,665 A | 3/1988 | Palmaz |
| 4,748,982 A | 6/1988 | Horzewski et al. |
| 5,451,233 A | 9/1995 | Yock |

FOREIGN PATENT DOCUMENTS

DE 38 23 060 A1 1/1989

OTHER PUBLICATIONS

Ballondilation und koronare Gefäβstützenimplantation, Erbel, R., Schatz, R., Dietz, U., Nixdorff, U., Haude, M., Aichinger, S., Pop, T., and Meyer, J., Z Kardiol 78:71–77 (1989).
English translation of cited section of Ballondilation und koronare Gefäβstützenimplantation, Erbel, R., Schatz, R., Dietz, U., Nixdorff, U., Haude, M., Aichinger, S., Pop, T., and Meyer, J., Z Kardiol 78:71–77 (1989).
English language abstract of DE 38 23 060 A1.

*Primary Examiner*—Beverly M. Flanagan

(57) ABSTRACT

A stent delivery assembly includes a catheter for carrying an intravascular stent for use in a body lumen. The catheter assembly includes a rapid exchange feature in which a proximal port is spaced a relatively short distance from the distal end of the catheter and a relatively long distance from the proximal end of the catheter. A stent is mounted on the expandable member or balloon portion of the catheter.

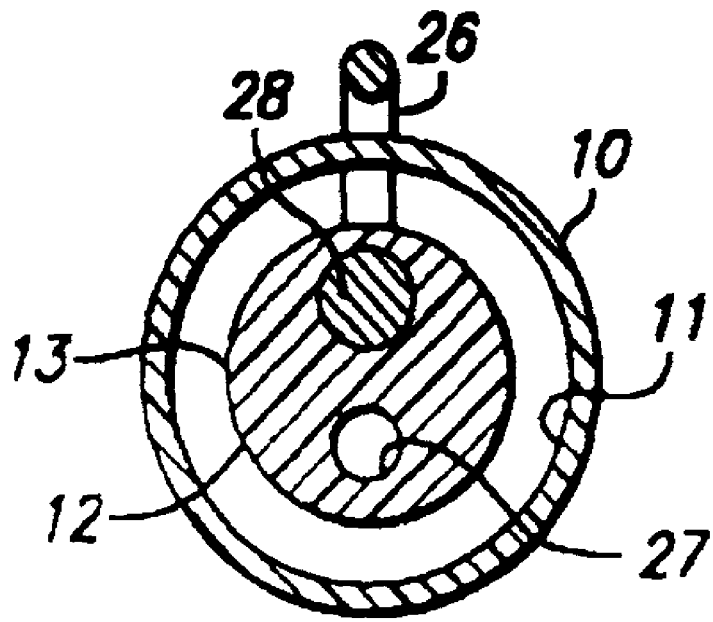

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–23 are cancelled.

* * * * *